(12) United States Patent
Miller et al.

(10) Patent No.: US 7,485,324 B2
(45) Date of Patent: Feb. 3, 2009

(54) USE OF EXOGENOUS GASEOUS NITRIC OXIDE IN THE TREATMENT AND DISINFECTION OF BIOFILMS

(75) Inventors: Chris Miller, North Vancouver (CA); Abdi Ghaffari, Edmonton (CA); Ali Ardakani, Edmonton (CA); Bruce Murray, Tofield (CA); Doug Hole, Edmonton (CA)

(73) Assignee: Pulmonox Technologies Corporation (CA)

( * ) Notice: Subject to any disclaimer, the term of this patent is extended or adjusted under 35 U.S.C. 154(b) by 0 days.

(21) Appl. No.: 10/953,827

(22) Filed: Sep. 29, 2004

(65) Prior Publication Data

US 2006/0068031 A1 Mar. 30, 2006
US 2008/0233212 A9 Sep. 25, 2008

Related U.S. Application Data

(60) Provisional application No. 60/506,807, filed on Sep. 29, 2003.

(51) Int. Cl.
*A61K 33/00* (2006.01)
*A01N 25/00* (2006.01)
*A01N 59/00* (2006.01)

(52) U.S. Cl. ...................... 424/718; 424/405
(58) Field of Classification Search ................. 424/718, 424/405; 423/405
See application file for complete search history.

(56) References Cited

U.S. PATENT DOCUMENTS 5,957,880 A 9/1999 Igo
6,432,077 B1 8/2002 Stenzler

OTHER PUBLICATIONS

Shank et al. The Effect of Nitric Oxide on Bacteria Appl. Microbiol. 1962, 10, 185-189.*
Mancinelli et al. Effects of Nitric Oxide and Nitrogen Dioxide on Bacterial Growth Appl. and Environmental Microbiol. 1983, 46 (1), 198-202.*
Zeuch et al. Abstract DE003713396A1 Nov. 10, 1998.*
Schmidt et al. Journal of Bacteriology May 2004, 186(9), 2781-2788.*
Miller et al. Journal of Cutaneous Medicine and Surgery 2004, 8(4), 233-238.*
Abstract; Mansch et al. ASTM Special Technical Publication 1994, 203-16; 1 page.*
English language abstract of Han et al. KR 202066 1 page.*
Han et al. KR 202066 Jun. 15, 1999 pp. 1-10.*

* cited by examiner

*Primary Examiner*—Sreeni Padmanabhan
*Assistant Examiner*—Ernst V Arnold
(74) *Attorney, Agent, or Firm*—Carissa A. Tener

(57) ABSTRACT

The administration of gaseous nitric oxide as a biocidal moiety is proffered as a de novo treatment in the control and eradication of biofilms. The present invention relates to the use or methods of application of exogenous nitric oxide gas (gNO) as a stand alone biocidal agent or in cohort with any or all adjunct vehicles in the control of biofilms generated by microbial organisms, i.e., bacteria, protozoa, amoeba, fungi etc. Further, the present invention introduces the concept of utilization and methods of application of gaseous nitric oxide in control and eradication of biofilm forming microorganisms. Noteworthy areas of application are offered as examples. They include, and are not limited to, air and/or water heating/cooling distribution systems in facilities such as hospitals and laboratories, surfaces of medical devices, household surfaces, dental plaque, dental and/or medical water treatment lines, industrial pipelines, water treatment and distribution facilities and fluids sterilization. Various specialized delivery apparatus will be designed to facilitate nitric oxide gas administration to each specific unique application.

26 Claims, 9 Drawing Sheets

USE OF EXOGENOUS GASEOUS NITRIC OXIDE IN THE TREATMENT AND DISINFECTION OF BIOFILMS

CLAIM OF PRIORITY

This application claims priority to U.S. provisional patent application Ser. No. 60/506,807, which was filed on Sep. 29, 2003.

FIELD OF THE INVENTION

The present invention generally relates to a methodology for obtunding biofilms.

BACKGROUND OF INVENTION

Microbial organisms are capable of adhering to a surface aggregate in a polymer-like matrix. This is referred to as a biofilm and is synthesized endogenously by the microbe(s). Biofilms are ubiquitous in nature and are commonly found in a wide range of environments including domestic and industrial water systems. Biofilms are also etiologic agents for a number of disease states in mammals. Otitis media, dental plaque, bacterial endocarditis, cystic fibrosis and Legionnair's disease along with a broad array of hospital acquired, dental and medical clinic infections are examples of its pathology. Bacteria growing in biofilms display increased resistance to antibiotics. Commonly surveyed microbial organisms that form biofilms are *Burkholderia cenocepacia, Staphlococcus, Steptococccus, Pseudomonas*, and *Legionnella* and their subtypes.

In U.S. Pat. No. 5,957,880, Igo taught that adding nitric oxide to blood within an extracorporeal system is known to inhibit platelet activation. Our summary of Igo's '880 reference is based on Igo's teaching which is as follows (bracketed material is added and underlining was added for emphasis):

Referring to FIG. 1, a typical CPB circuit is indicated generally by reference numeral 10. The patient is shown by numeral 12. A venous cannula 13 inserted into the patient is connected into a fluid inlet tube 14 that directs blood from the patient to a venous reservoir 18. Another cannula 15 inserted in the patient is connected to another fluid inlet 16 that also leads from the patient to venous reservoir 18. Reservoir 18 may be a pole mounted unit or may be located on the heart-lung machine table, but in either case normally is the first fixed point in the circuit, lines 14 and 16 normally being flexible and long enough to allow surgeon and surgical assistants room to maneuver around the surgical table. The purpose of venous reservoir 18 is to accumulate the admitted blood for feeding the balance of the CPB circuit. The accumulator eliminates pump starvation and cessation of pump prime by providing a buffer from ebb and flow of blood from the patient.

From the venous reservoir, plastic tubing 20 leads to the inlet side of a roller pump 22. Roller pump 22 has a hub 24 from which protrude two arms 26. These arms impinge on the tubing 20 collapsing it. Rotation of the pump hub 24 in the direction indicated by reference numeral 28 provides the desired flow direction and flow rate. The blood leaves the roller pump 22 through tubing 30 to the inlet of the oxygenator 32. The blood can be thermally adjusted by passing it from the oxygenator 32 through tubing 34 into a heat exchanger 36 for heating or cooling before returning to the oxygenator 32 by tubing 38. Upon oxygenation, the blood exits the oxygenator in two ways. The first way is through tubing 40 to another roller pump 42, from there pumped through tubing 44 to a cardioplegia system 46, then to the patient 12 through outlet tubing 47 and a cannula 48. The other mechanism with which the blood leaves the oxygenator 32 is through tubing 50. A filter 52 is located on a side branch of this portion of the circuit. When it is desired to use the filter 52, tubing 50 is clamped in the area noted by numeral 54 and the blood travels through the filter 52 before returning to the patient through outlet tubing 57 and a cannula 56. The venous return reservoir 18 is the juncture of all blood removed from the patient. It is at this location where the improvement according to this invention suitably may be added to the CPB circuit, prior to the pump 22 and the blood treatment oxygenator 32.

FIG. 2 depicts an extracorporeal blood treatment circuit in general, designated by reference numeral 11, and in which reference numerals are the same for the like elements found in the specific CPB circuit shown in FIG. 1. Reference numeral 41 represents a blood treatment component. In the case of a CPB apparatus as in FIG. 1, blood treatment component 41 comprises at least oxygenator 32 and optionally also heat exchanger 36 with connecting tubing 34, 38 and either or both of (1) the cardioplegia system 46 with associated second pump 42 and connecting tubing 40, 44, 47 and (2) the filter 52 with associated tubing 50. Numeral 17 indicates a blood fluid inlet generally and numeral 49 indicates a fluid outlet for blood return generally to the patient in FIG. 2. In accordance with this invention, blood treatment component 41 of the fluid circuit of the apparatus 11, instead of being an oxygenation system as in FIG. 1, suitably may be a heat exchange system 36, a renal dialysis component for exchange of urea and other blood chemicals with a dialysate solution across an exchange membrane, or an organ perfusion component such as an ex vivo liver and perfusion support system tying into circuit interconnects 30 and 49.

In accordance with this invention, one of more feeds of nitric oxide are employed, as necessary in the particular circuit, to maintain the concentration of nitric oxide in the circulating extracorporeal blood at a dosage effective to produce the desired inhibition of platelet activation over a period of time sufficient for the journey through the extracorporeal circulation apparatus yet insufficient to sustain the inhibition after the blood is returned to the patient and desired dosages. FIG. 3 depicts one such feed at the initial (venous inlet) portion of the circuit illustrated in FIG. 1. In this preferred embodiment of the invention, a gas permeable membrane 60 is located within a conduit 62 of the blood circuit located immediately downstream from the reservoir 18. The gas permeable membrane 60 is elongated and tubular in form and is disposed longitudinally within conduit 62 adapted to come into contact with blood flowing through conduit 62. A gaseous source, a mixture of nitric oxide and a carrier gas such as nitrogen, is housed in container 68 under high pressure. Regulator 66 controls the output gas pressure to periodic driver 69. The purpose of the periodic driver 69 is to induce a sinusoidal shaped pressure curve to the gas much like a "pulse". The gas leaves the driver through tubing 64 and flows into the interior of gas permeable membrane 60. Due to the permeability of this membrane 60 to nitric oxide gas, the gas will diffuse through the membrane and dissolve in the blood plasma where it will come into contact with platelets. The membrane is selected to be impermeable to nitrogen and the nitrogen carrier gas will not diffuse through the membrane. Coupled to the outlet of the membrane 60 is outlet tubing 61, which is connected to valve 63. Valve 63 adjusts the back pressure of the system. From the valve 63 the carrier gas and any residual nitric oxide gas is carried through tube 65 into container 67, which is filled with a scavenger liquid such as methylene blue. The gas mixture is allowed to bubble up through the container containing the scavenger liquid. The scavenger liquid absorbs any residual nitric oxide so that the only gas that escapes into the atmosphere is the carrier gas.

Blood guarded by dissolved nitric oxide exits conduit 62 and into tubing 20 where is passes by a conventional blood flow measuring device 90. Signals from blood flow measuring device 90 are transferred by line 92 to controller feedback logic component 94 which outputs a signal through line 96 to controller driver component 98 for controlling pressure and flow from regulator 66. The controller system comprising units 90, 94 and 98 with connecting lines 92 and 96 controls the flow of gas into membrane 60 in relation to the flow of blood through tubing 20. In this manner, when the flow rate of the blood is low, the nitric oxide introduction is correspondingly and automatically reduced. Conversely, in cases of high flow the nitric oxide introduction is correspondingly and automatically raised.

The gas permeable membrane 62 has a gas permeable rate K which is dependent on the material of construction and the molecular characteristics of the gas. For nitric oxide, the gaseous release rate from membrane 60 is proportional to K, the exposed surface of the membrane to the blood, the internal gaseous pressure within the membrane and the hydraulic pressure of and gas tension of nitric oxide (if any) in the blood flowing by it. Delivered molecular concentrations to the blood is [sic] calculated knowing the above plus the absorption coefficient of the blood to the nitric oxide. Thus the controller controls the gas flow and at a level which, for the characteristics of membrane 60 and the absorption coefficient of nitric oxide gas at the temperature of the blood in the apparatus (before thermal adjustment, if any), is sufficient to provide an actual concentration of nitric oxide in solution effective in the presence of venous red blood cell blood hemoglobin to inhibit platelet activation.

FIG. 4 illustrates a longitudinal sectional view of the conduit 62, the gas permeable membrane 60 and the tubing 64. Nitric oxide gas flows into the membrane 60 at location 70. As the gas pressure inside the gas permeable membrane 60 exceeds the pressure of the blood within conduit 62, nitric oxide gas will diffuse from the membrane into the blood stream as indicated by arrows 74. The nitric oxide will be absorbed by the blood cellular components which will mediate the inflammatory response as described earlier.

Referring to FIG. 5, which illustrates a cross section of FIG. 3 along the line A-A, the relationship between the geometry's of the conduit 62 and gas permeable membrane 60 is as follows. The cross sectional area of the inside of conduit 62 minus the sectional area of the gas permeable membrane 60 (such difference being referenced by numeral 76) is approximately equivalent to the cross section of the tubing elsewhere in the CPB circuit, (i.e. the cross section of tubing element 20). With this relationship the blood is not subjected to an adverse pressure gradient in conduit 62. Longitudinally, the shape of the gas permeable membrane 60 follows that of the conduit 62, again so that adverse pressure gradients are not imparted into the circuit.

FIG. 6 illustrates another preferred embodiment of the invention. In this embodiment a carrier gas is not used so that container 68 holds a 100% concentration of nitric oxide. A pulse drive generator 69 is not shown but may be present. In this embodiment, there is no outlet conduit of membrane 60. As pressure builds up in conduit 60, the nitric oxide diffuses into the bloodstream as previously described. Because there are no residual carrier gas molecules, there is no need for a return. Simply stated, components 61, 63, 65, and 67 of the embodiment depicted in FIG. 2 are absent at the distal end of membrane 60 and the tube 62 in this configuration. As in the embodiment depicted in FIG. 3, a controller comprising components 90, 94 and 98 with connections 92 and 96 controls the concentration of nitric oxide in solution in the blood. FIG. 8 illustrates a cross sectional view B-B of FIG. 7 with the same numbers used in the same way as in FIG. 5.

The above embodiments illustrate an optimal configuration of the invention in which the blood flows around the external portion of a gas permeable membrane 60. While it is within the scope of this invention that the system can be configured so that the gas is on the external portion of the membrane and blood is flowed within the membrane, in low gas pressure conditions some membranes dilate, increasing the cross sectional area of the membrane and lowering blood flow through that portion of the apparatus, and in high gas pressure conditions, some membranes might collapse, reducing blood flow. In the preferred embodiments, if gas flow is zero, the membrane might collapse but it would not occlude or preclude blood flow.

FIG. 9 depicts another embodiment of the [Igo] invention. In this embodiment the nitric oxide feed is to reservoir 18. The feed comprises a diffuser 100 for diffusing nitric oxide gas into the reservoir, and comprises a regulator 66 for controlling gas pressure and rate of flow into the reservoir and a driver 69 for delivering the nitric oxide gas into reservoir 18 through inlet 64 in a pulsatile manner. Suitably diffuser 100 comprises a membrane or filter 80 that is not permeable to blood and is permeable to nitric oxide gas through which nitric oxide gas is introduced into the reservoir. As in the embodiment depicted in FIGS. 3 and 6, a controller comprising components 90, 94 and 98 with connections 92 and 96 controls the concentration of nitric oxide in solution in the blood.

It is important that the location of the nitric oxide feed be close to the patient cannulation point as possible in the extracorporeal circuit to reduce so much as practicable the period of exposure of platelets to non-endothelial surfaces. At least one feed location is described generally as upstream of the pump that is needed to circulate the blood extracorporeally through the system and back to the patient. With reference to the FIG. 2, that point is anywhere in line 15. In FIGS. 3-9, which involve a CPB circuit where blood from two inlets 14 and 16 is pooled in reservoir 18, either the reservoir or the tubing immediately past the reservoir is selected for initial introduction of the nitric oxide, for the practical reason that these are the closest stationary locations in the system to the patient source of blood and also because control of nitric oxide introduction is most readily accomplished in the reservoir or in the blood filled lines in the immediately downstream tubing under the influence of a pump as opposed to in the blood inlet lines where lines are mobile to allow access to the surgical field, and especially in the case of blood suctioned from the operative field where intermittent blood and air flow occurs. The closest stationary location will vary according to the blood treatment component 41 involved in the use of this invention. Because of the very short half life of nitric oxide in the blood, additional feeds may be used further downstream to maintain the desired nitric oxide concentration in the blood without overdosing the blood in but one location.

In other words, Igo teaches away from adding nitric oxide to blood to combat pathogens.

In U.S. Pat. No. 6,432,077, Stenzler teaches that topical application of nitric oxide to wounds and/or skin of mammals is beneficial to wound healing because it decreases further infection. No where does Stenzler teach, disclose or suggest exposing nitric oxide to blood to combat pathogens. Our summary of Stenzler is based on his disclosure, which reads as follows:

The treatment of infected surface or subsurface lesions in patients has typically involved the topical or systemic administration of anti-infective agents to a patient. Antibiotics are one such class of anti-infective agents that are commonly used to treat an infected abscess, lesion, wound, or the like. Unfortunately, an increasingly number of infective agents such as bacteria have become resistant to conventional antibiotic therapy. Indeed, the increased use of antibiotics by the medical community has led to a commensurate increase in resistant strains of bacteria that do not respond to traditional or even newly developed anti-bacterial agents. Even when new anti-infective agents are developed, these agents are extremely expensive and available only to a limited patient population.

Another problem with conventional anti-infective agents is that some patients are allergic to the very compounds necessary to their treat their infection. For these patients, only few drugs might be available to treat the infection. If the patient is infected with a strain of bacteria that does not respond well to substitute therapies, the patient's life can be in danger.

A separate problem related to conventional treatment of surface or subsurface infections is that the infective agent interferes with the circulation of blood within the infected region. It is sometimes the case that the infective agent causes constriction of the capillaries or other small blood vessels in the infected region which reduces bloodflow. When bloodflow is reduced, a lower level of anti-infective agent can be delivered to the infected region. In addition, the infection can take a much longer time to heal when bloodflow is restricted to the infected area.

This increases the total amount of drug that must be administered to the patient, thereby increasing the cost of using such drugs. Topical agents may sometimes be applied over the infected region. However, topical anti-infective agents do not penetrate deep within the skin where a significant portion of the bacteria often reside. Topical treatments of anti-infective agents are often less effective at eliminating infection than systemic administration (i.e., oral administration) of an anti-infective pharmaceutical.

In the 1980's, it was discovered by researchers that the endothelium tissue of the human body produced nitric oxide (NO), and that NO is an endogenous vasodilator, namely, and agent that widens the internal diameter of blood vessels. NO is most commonly known as an environmental pollutant that is produced as a byproduct of combustion. At high concentrations, NO is toxic to humans. At low concentrations, researchers have discovered that inhaled NO can be used to treat various pulmonary diseases in patients. For example, NO has been investigated for the treatment of patients with increased airway resistance as a result of emphysema, chronic bronchitis, asthma, adult respiratory distress syndrome (ARDS), and chronic obstructive pulmonary disease (COPD).

NO has also been investigated for its use as a sterilizing agent. It has been discovered that NO will interfere with or kill the growth of bacteria grown in vitro. PCT International Application No. PCT/CA99/01123 published Jun. 2, 2000 discloses a method and apparatus for the treatment of respiratory infections by NO inhalation. NO has been found to have either an inhibitory and/or a cidal effect on pathogenic cells.

While NO has shown promise with respect to certain medical applications, delivery methods and devices must cope with certain problems inherent with gaseous NO delivery. First, exposure to high concentrations of NO is toxic, especially exposure to NO in concentrations over 1000 ppm. Even lower levels of NO, however, can be harmful if the time of exposure is relatively high.

For example, the Occupational Safety and Health Administration (OSHA) has set exposure limits for NO in the workplace at 25 ppm time-weighted averaged for eight (8) hours. It is extremely important that any device or system for delivering NO include features that prevent the leaking of NO into the surrounding environment. If the device is used within a closed space, such as a hospital room or at home, dangerously high levels of NO can build up in a short period of time.

Another problem with the delivery of NO is that NO rapidly oxidizes in the presence of oxygen to form $NO_2$, which is highly toxic, even at low levels. If the delivery device contains a leak, unacceptably high levels $NO_2$ of can develop. In addition, to the extent that NO oxides to form $NO_2$, there is less NO available for the desired therapeutic effect. The rate of oxidation of NO to $NO_2$ is dependent on numerous factors, including the concentration of NO, the concentration of $O_2$, and the time available for reaction. Since NO will react with the oxygen in the air to convert to $NO_2$, it is desirable to have minimal contact between the NO gas and the outside environment.

Accordingly, there is a need for a device and method for the treatment of surface and subsurface infections by the topical application of NO. The device is preferably leak proof to the largest extent possible to avoid a dangerous build up of NO and $NO_2$ concentrations. In addition, the device should deliver NO to the infected region of the patient without allowing the introduction of air that would otherwise react with NO to produce $NO_2$. The application of NO to the infected region preferably decreases the time required to heal the infected area by reducing pathogen levels. The device preferably includes a NO and $NO_2$ absorber or scrubber that will remove or chemically alter NO and $NO_2$ prior to discharge of the air from the delivery device.

In a first aspect of the [Stenzler] invention, a device for the topical delivery of nitric oxide gas to an infected area of skin includes a source of nitric oxide gas, a bathing unit, a flow control valve, and a vacuum unit. The bathing unit is in fluid communication with the source of nitric oxide gas and is adapted for surrounding the area of infected skin and forming a substantially air-tight seal with the skin surface. The flow control valve is positioned downstream of the source of nitric oxide and upstream of the bathing unit for controlling the amount of nitric oxide gas that is delivered to the bathing unit.

The vacuum unit is positioned downstream of the bathing unit for withdrawing gas from the bathing unit.

In a second aspect of the [Stenzler] invention, the device according to the first aspect of the invention includes a controller for controlling the operation of the flow control valve and the vacuum unit.

In a third aspect of the [Stenzler] invention, the device according to the first aspect of the invention further includes a source of dilutent gas and a gas blender. The dilutent gas and the nitric oxide gas are mixed by the gas blender. The device also includes a nitric oxide gas absorber unit that is positioned upstream of the vacuum unit. The device also includes a controller for controlling the operation of the flow control valve and the vacuum unit.

In a fourth aspect of the [Stenzler] invention, a method of delivering an effective amount of nitric oxide to an infected area of skin includes the steps of providing a bathing unit around the infected area of skin, the bathing unit forming a substantially air-tight seal with the skin. Gas containing nitric oxide is then transported to the bathing unit so as to bathe the infected area of skin with gaseous nitric oxide.

Finally, at least a portion of the nitric oxide gas is evacuated from the bathing unit.

It is an object of the [Stenzler] invention to provide a delivery device for the topical delivery of a NO-containing gas to an infected area of skin. It is a further object of the device to prevent the NO-containing gas from leaking from the delivery device. The method of delivering an effective amount of nitric oxide gas to the infected area of skin kills bacteria and other pathogens and promotes the healing process.

As clearly illustrated, Stenzler never taught, suggested, nor disclosed exposing blood to NO to destroy pathogens.

In 1989 it was discovered that nitric oxide was produced by the endothelium tissue of mammals. It has since been demonstrated that endogenous nitric oxide is a potent modulator for a number of systemic functions in mammals including selective pulmonary vasodilatation, neurotransmission and cytoxic activity over a wide range of microorganisms including bacteria and viruses. Nitric oxide has been known for years as an environmental pollutant and is toxic to mammals at high doses. At minimal concentrations however exogenously supplied (eg. <100 ppm) nitric oxide has selectively been used to treat human patients with a wide range of pulmonary diseases including, but not limited to, chronic bronchitis, asthma, ARDS (Acute Respiratory Disease Syndrome) etc. Nitric oxide has also found utility in its application as both a sterilizing agent and as a bactericidal agent for pathogenic organisms.

Septicemia is a serious, rapidly progressive, life-threatening infection that can arise from infections throughout the body, including infections in the lungs, abdomen, and urinary tract. It may precede or coincide with infections of the bone (osteomyelitis), central nervous system (meningitis), or other tissues. Septicemia can rapidly lead to septic shock and death. Septicemia associated with some organisms such as meningococci can lead to shock, adrenal collapse and disseminated intravascular coagulopathy.

In all examples referenced there is a dosage range of nitric oxide application that needs to be maintained in order to establish efficacy. Accordingly the employment of nitric oxide as a dissolved gas or through selective nitric oxide donors in an extracorporeal circuit allows for the titration of exogenously administered nitric oxide levels required to optimize the therapeutic antimicrobial and bactericidal benefits.

The impact from lost industrial productivity along with its significant impact on the public health sector makes the eradication of biofilms a major goal.

SUMMARY OF INVENTION

The antimicrobial properties of nitric oxide as a molecule have been well documented. The administration of gaseous nitric oxide as a biocidal moiety is proffered as a de novo treatment in the control and eradication of biofilms. The present invention relates to the use or methods of application of exogenous nitric oxide gas (gNO) as a stand alone biocidal agent or in cohort with any or all adjunct vehicles in the control of biofilms generated by microbial organisms i.e. bacteria, protozoa, amoeba, fungi etc. Further, the present invention introduces the concept of utilization and methods of application of gaseous nitric oxide in control and eradication of biofilm forming microorganisms. Noteworthy areas of application are offered as examples. They include, and are not limited to, air and/or water heating/cooling distribution systems in facilities such as hospitals and laboratories, surfaces of medical devices, household surfaces, dental plaque, dental and/or medical water treatment lines, industrial pipelines, water treatment and distribution facilities and fluids sterilization. Various specialized delivery apparatus will be designed to facilitate nitric oxide gas administration to each specific unique application.

The foregoing and additional advantages and characterizing features of the present invention will become clearly apparent upon reading of the ensuing detailed description together with the included experimental model wherein:

DETAILED DESCRIPTION OF THE INVENTION

Figure 1:
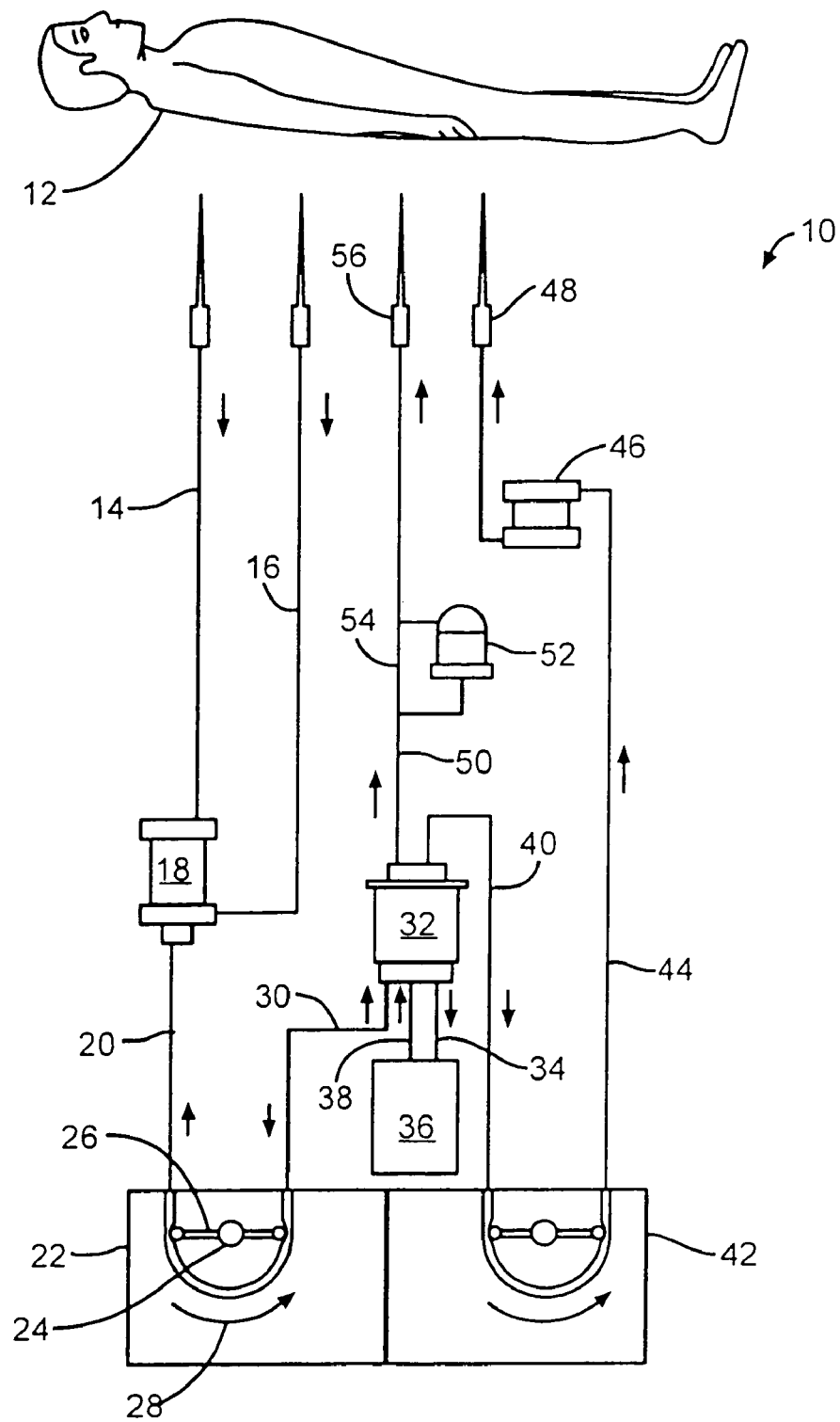
FIGS. 1-8 are prior art.
Figure 2:
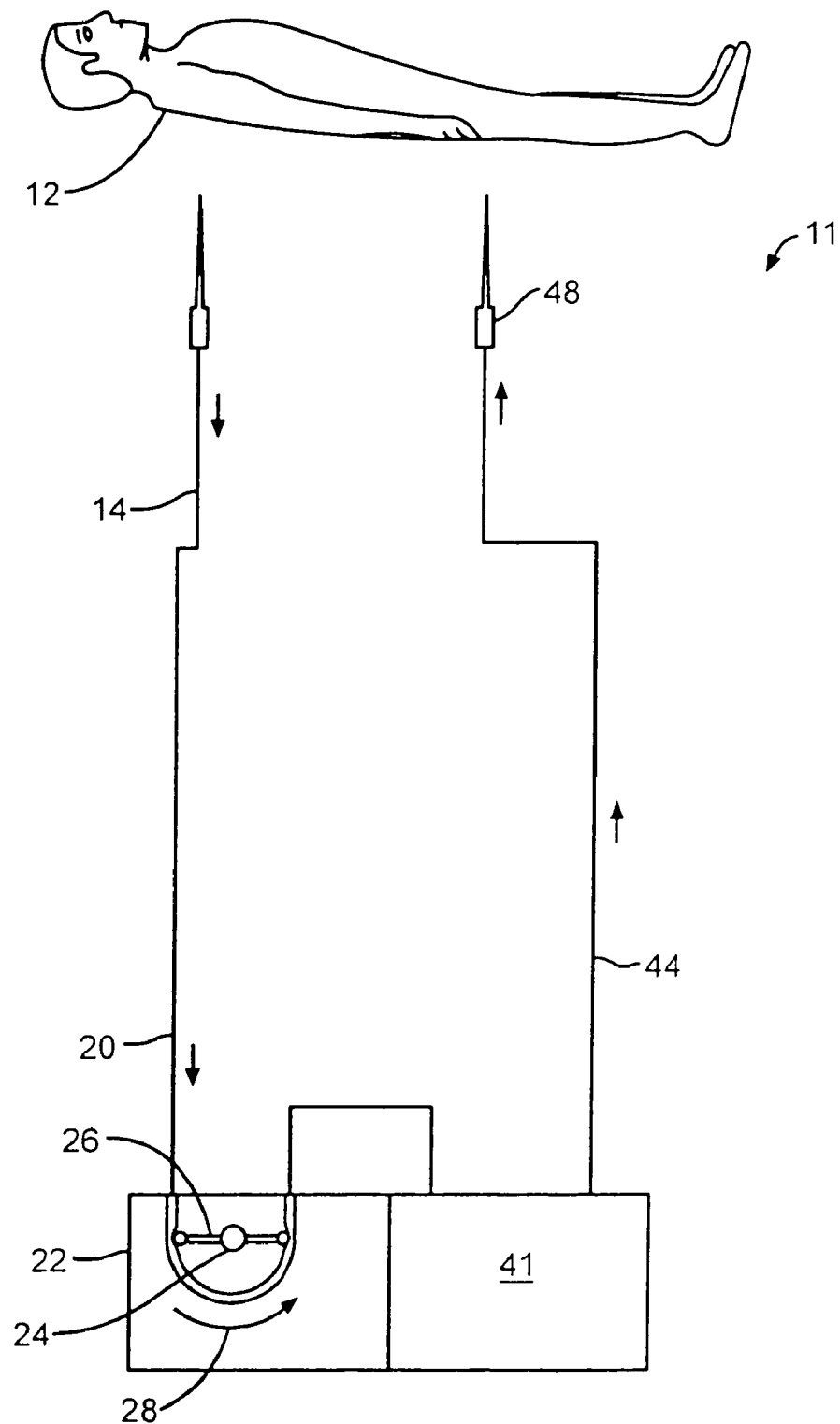
Figure 3:
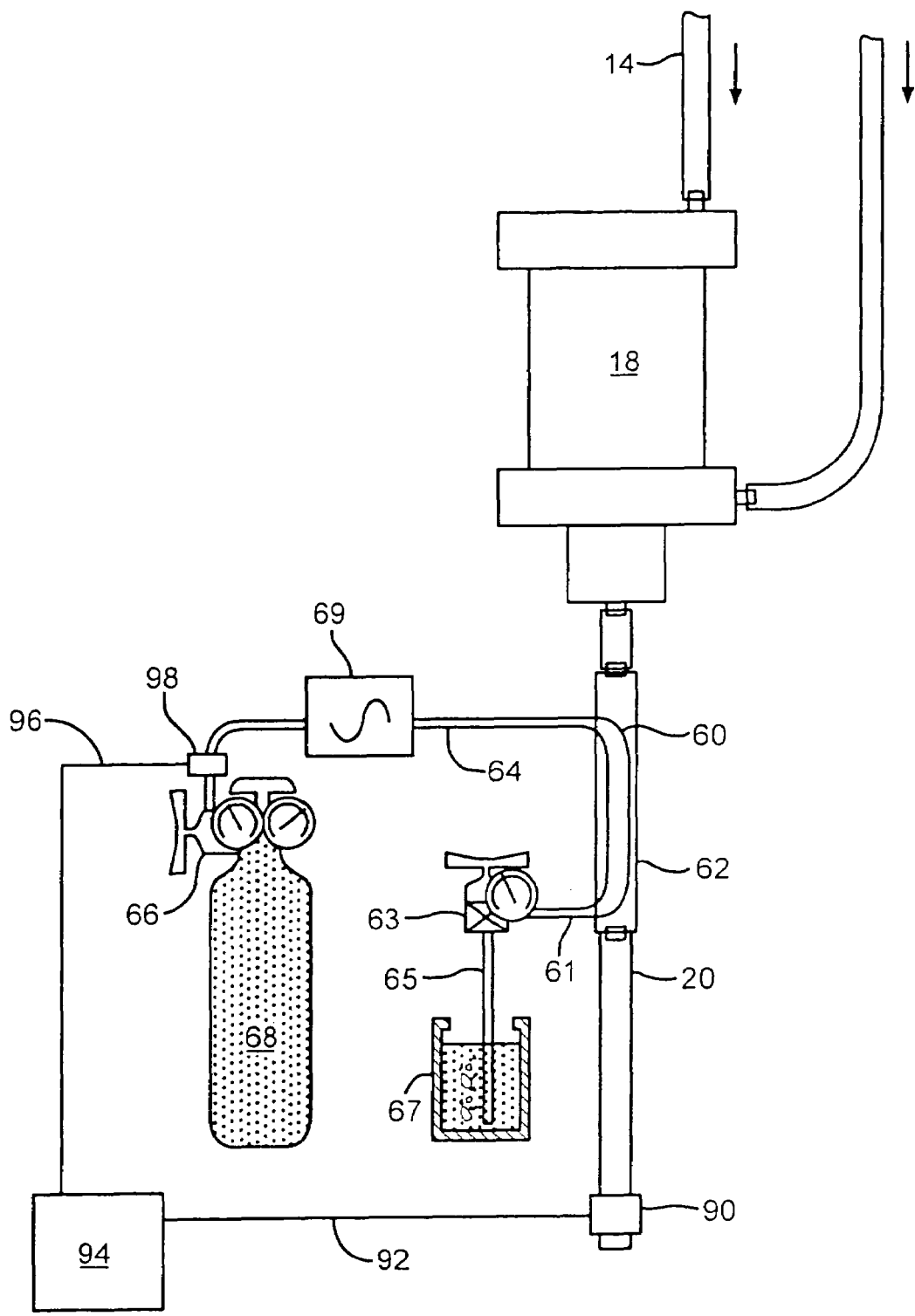
Figure 4:
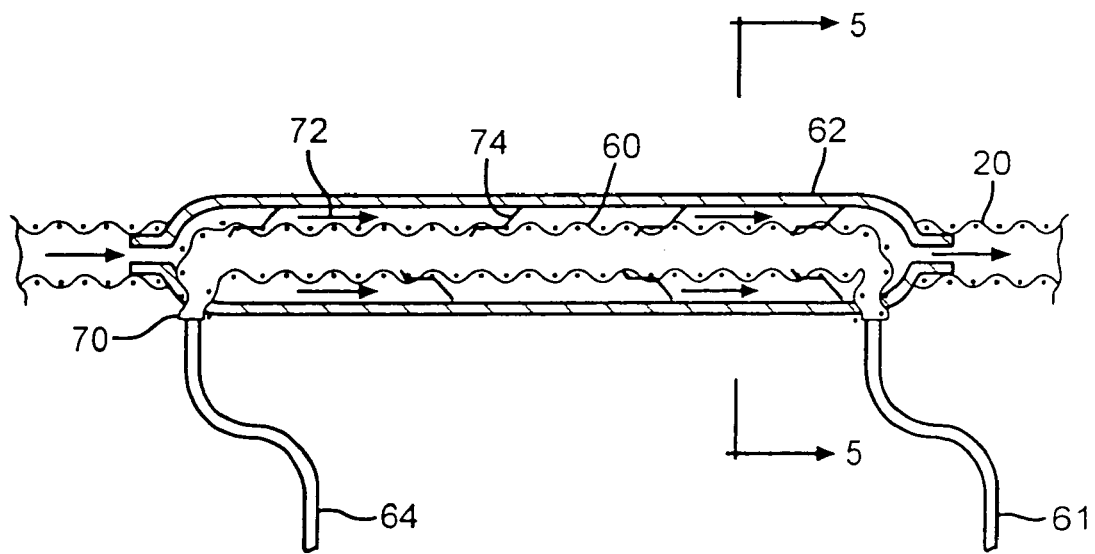
Figure 5:
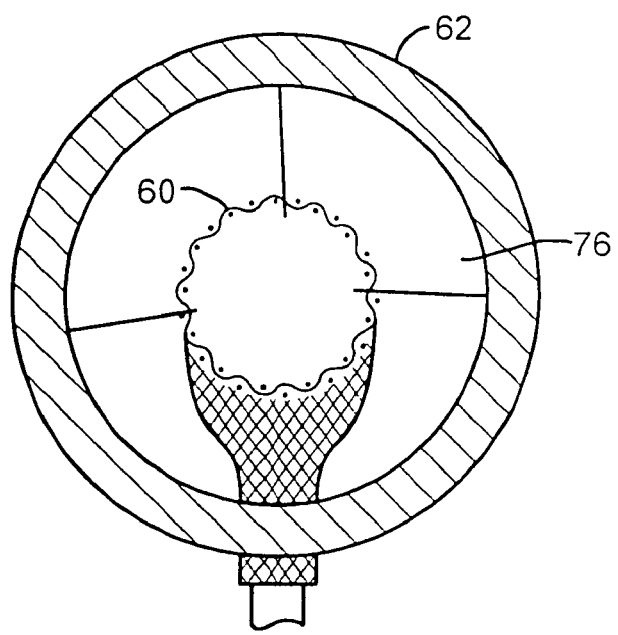
Figure 6:
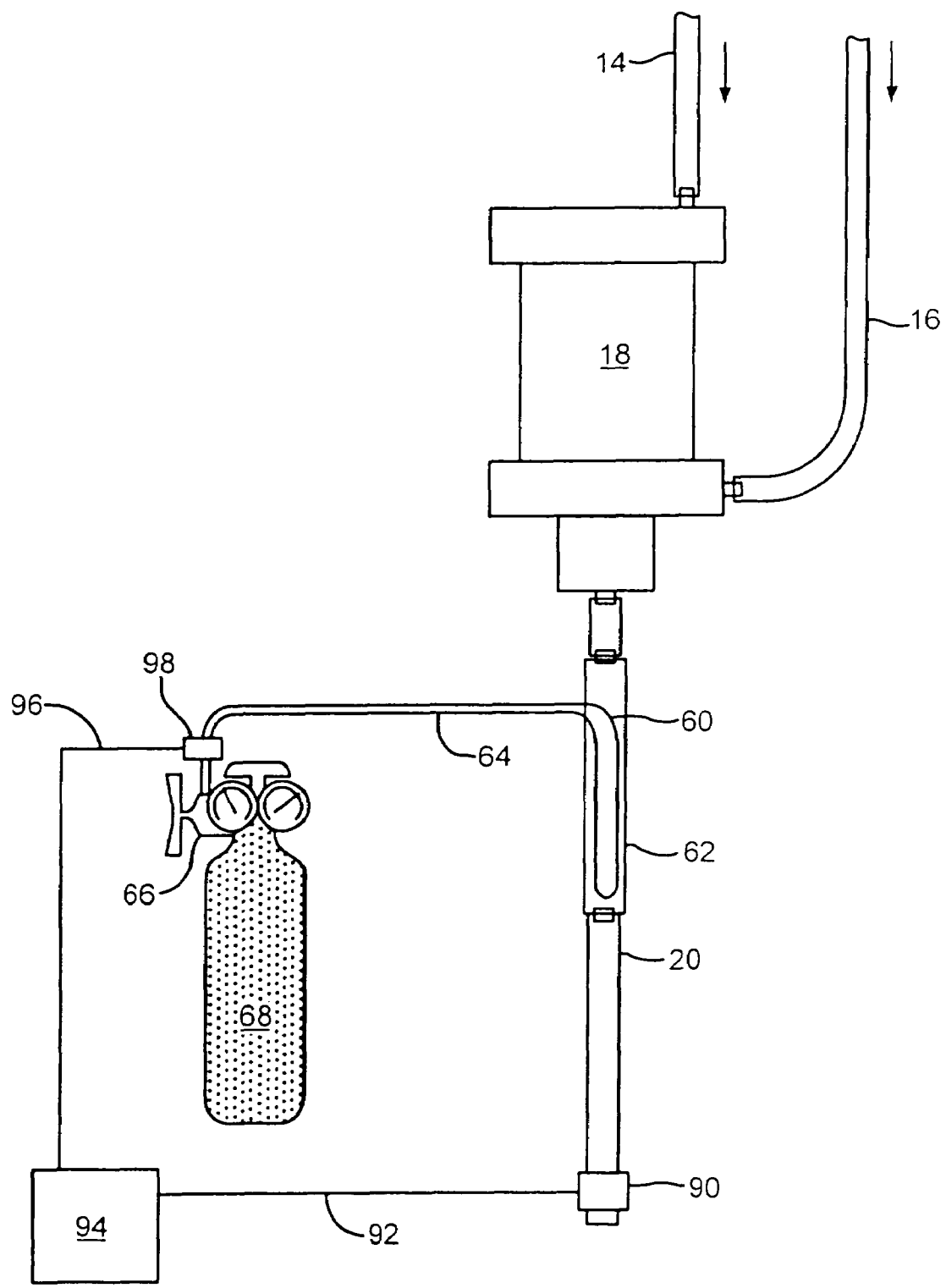
Figure 7:
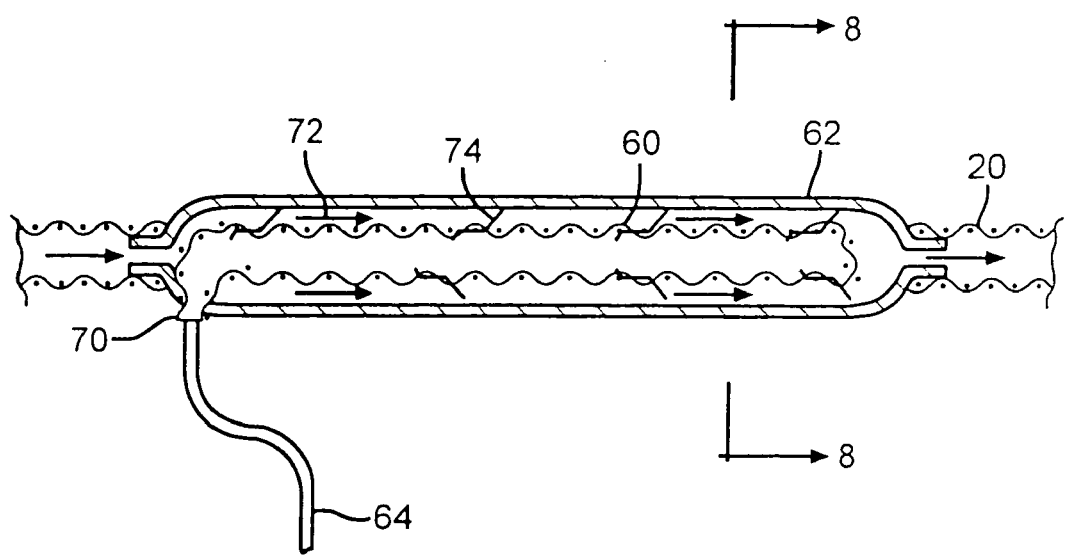
Figure 8:
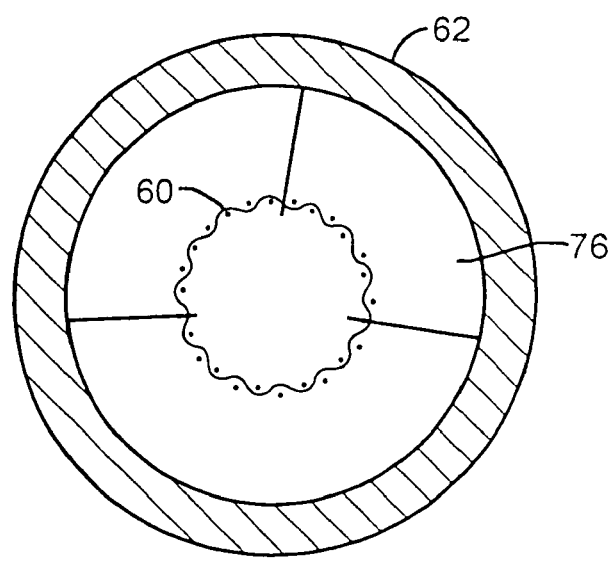
Figure 9:
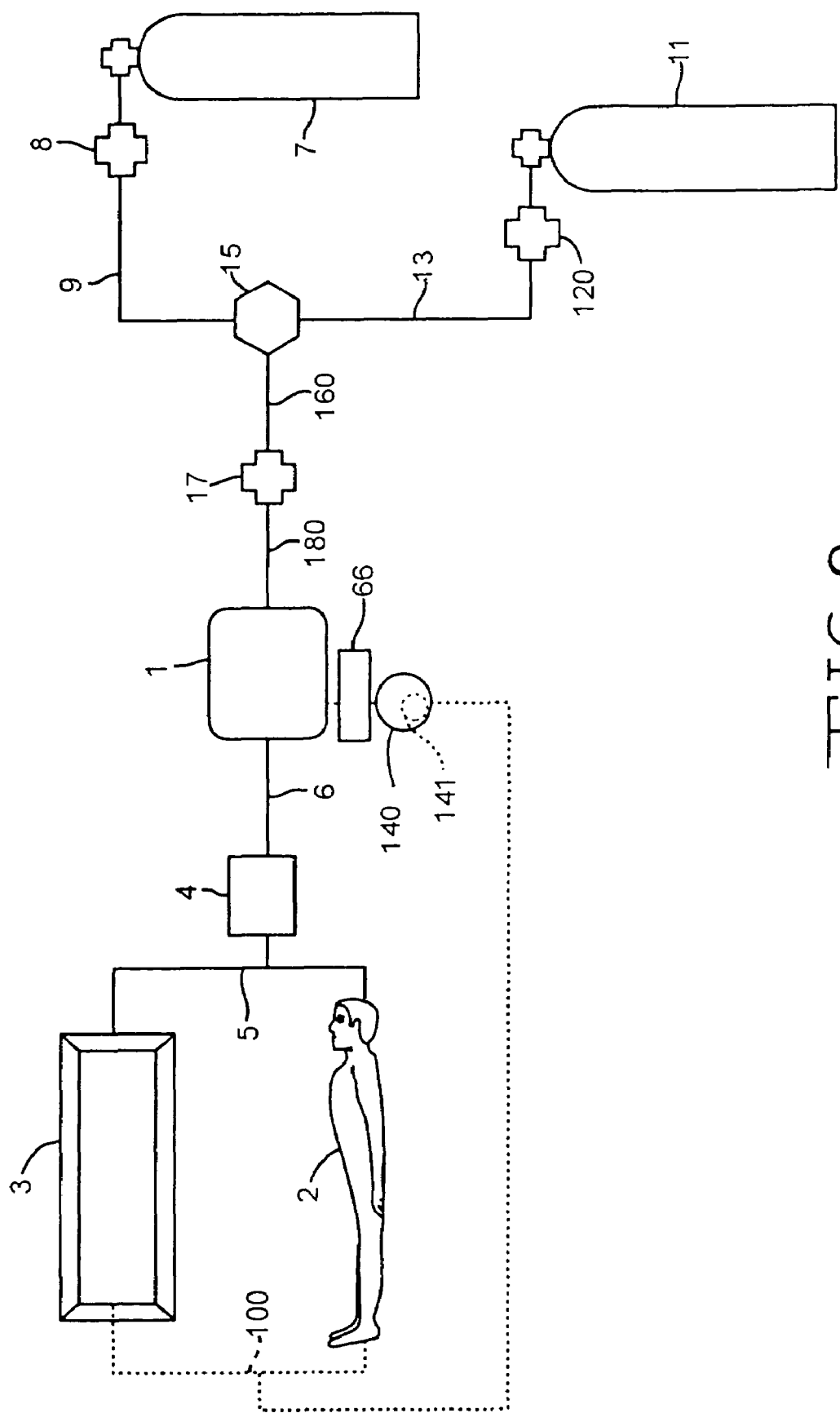
FIG. 9 is a schematic of the present invention.

The administration of gaseous nitric oxide is viewed as a novel biocidal agent in the efficacious management of numerous biofilm-forming microorganisms with particular emphasis on antibiotic resistant bacteria. The gNO can be administered through a variety of mechanisms. Examples of said administration of gNO are set forth in commonly assigned U.S. patent application Ser. No. 10/658,665. In that application, it was reported the examples are as follows:

Referring now to FIG. 9, a gaseous nitric oxide (NO) delivery device 1 is shown connected to a source of infected blood from either a patient 2 or a stored blood source 3, and a pumping system 4, through lines 5, 6.

The nitric oxide (NO) source 7, can be a pressurized cylinder containing nitric oxide (NO) gas, and a nitric oxide flow control valve/pressure regulator 8, delivering nitric oxide (NO) to the gaseous nitric oxide delivery device 1 through supply tubing 9 and an optional gas blender 15. The infected blood is then exposed to a controlled amount of nitric oxide (NO) by the gaseous nitric oxide (NO) delivery device 1, and the treated blood is then returned to either a patient 2 or a stored blood source 3, through line 100. The treated blood can still carry the nitric oxide when it returns to the patient or the stored blood source. By carrying a sufficient quantity of nitric oxide into the patient, which is completely contrary to the teaching of Igo, the nitric oxide can reduce the pathogens throughout the whole body of the patient.

In FIG. 9, the nitric oxide (NO) gas source 7 is a pressurized cylinder containing nitric oxide (NO) gas. While the use of a pressurized cylinder is the preferable method of storing the nitric oxide (NO) containing gas source 7, other storage and delivery means, such as a dedicated feed line can also be used. Typically the nitric oxide (NO) gas source 7 is a mixture of $N_2$ and NO. While $N_2$ is typically used to dilute the concentration of NO within the pressurized cylinder, any inert gas can also be used.

When the NO gas source 7 is stored in a pressurized cylinder, it is preferable that the concentration of NO in the pressurized cylinder fall within the range of about 800 ppm to about 1200 ppm. Commercial nitric oxide manufacturers typically produce nitric oxide mixtures for medical use at around the 1000 ppm range. Extremely high concentrations of NO are undesirable because accidental leakage of NO gas is more hazardous, and high partial pressures of NO tends to cause the spontaneous degradation of NO into nitrogen. Pressurized cylinders containing low concentrations of NO (i.e., less than 100 ppm NO) can also be used in accordance the device and method disclosed herein. Of course, the lower the concentration of NO used, the more often the pressurized cylinders will need replacement.

FIG. 9 also shows source of diluent gas 11 as part of the NO delivery device 1 that is used to dilute the concentration of nitric oxide (NO) for delivery to the gaseous nitric oxide (NO) delivery device 1 through line 13. The source of diluent gas 11 can contain $N_2$, $O_2$, air, an inert gas, or a mixture of these gases. It is preferable to use a gas such as $N_2$ or an inert gas to dilute the NO concentration since these gases will not oxidize the nitric oxide (NO) into $NO_2$, as would $O_2$ or air. The source of diluent gas 11 is shown as being stored within a pressurized cylinder. While the use of a pressurized cylinder is shown in FIG. 9 as the means for storing the source of diluent gas 11, other storage and delivery means, such as a dedicated feed line can also be used. The nitric oxide (NO) gas from the nitric oxide (NO) gas source 7 and the diluent gas from the diluent gas source 11 preferably pass through flow control valve/pressure regulators 8, 120, to reduce the pressure of gas that is admitted to the gaseous nitric oxide (NO) delivery device 1. The respective gas streams pass via tubing 9, 13, to an optional gas blender 15. The gas blender 15 mixes the nitric oxide (NO) gas and the diluent gas to produce a nitric oxide (NO)-containing gas that has a reduced concentration of nitric oxide (NO). Preferably, the nitric oxide (NO)-containing gas that is output from the gas blender 15 has a concentration that is less than about 200 ppm. Even more preferably, the concentration of nitric oxide (NO)-containing gas that is output from the gas blender 15 is less than about 100 ppm. The nitric oxide (NO)-containing gas that is output from the gas blender 15 travels via tubing 160 to a flow control valve 17. The flow control valve 17 can include, for example, a proportional control valve that opens (or closes) in a progressively increasing (or decreasing if closing) manner. As another example, the flow control valve 17 can include a mass flow controller. The flow control valve 17 controls the flow rate of the nitric oxide (NO)-containing gas that is input to the gaseous nitric oxide (NO) delivery device 1. The nitric oxide (NO)-containing gas leaves the flow control valve 17 via flexible tubing 180. The flexible tubing 180 attaches to an inlet of the gaseous nitric oxide (NO) delivery device 1. The inlet for 1 might include an optional one-way valve that prevents the backflow of gas.

In one preferred embodiment of the invention, the gaseous nitric oxide (NO) delivery device unit 1 includes an NO sensor 140 that measures the concentration of nitric oxide (NO) in the treated blood or fluid stream. The nitric oxide (NO) sensor 140 and nitric dioxide sensor (15) preferably report the concentrations of NO and $NO_2$ to a controller within the gaseous nitric oxide (NO) delivery device 1, for source gas flow control and alarm. The sensors, 140, 15, can be chemilluminesence-type, electrochemical cell-type, or spectrophotomentric type sensors.

In a similar embodiment, the present invention takes the nitric oxide gas composition in line 18 and directs the nitric oxide gas composition into a patient's breathing orifice, like a nose and/or mouth. The delivery device can be a conventional gas mask or plastic tubing.

Figure 10:
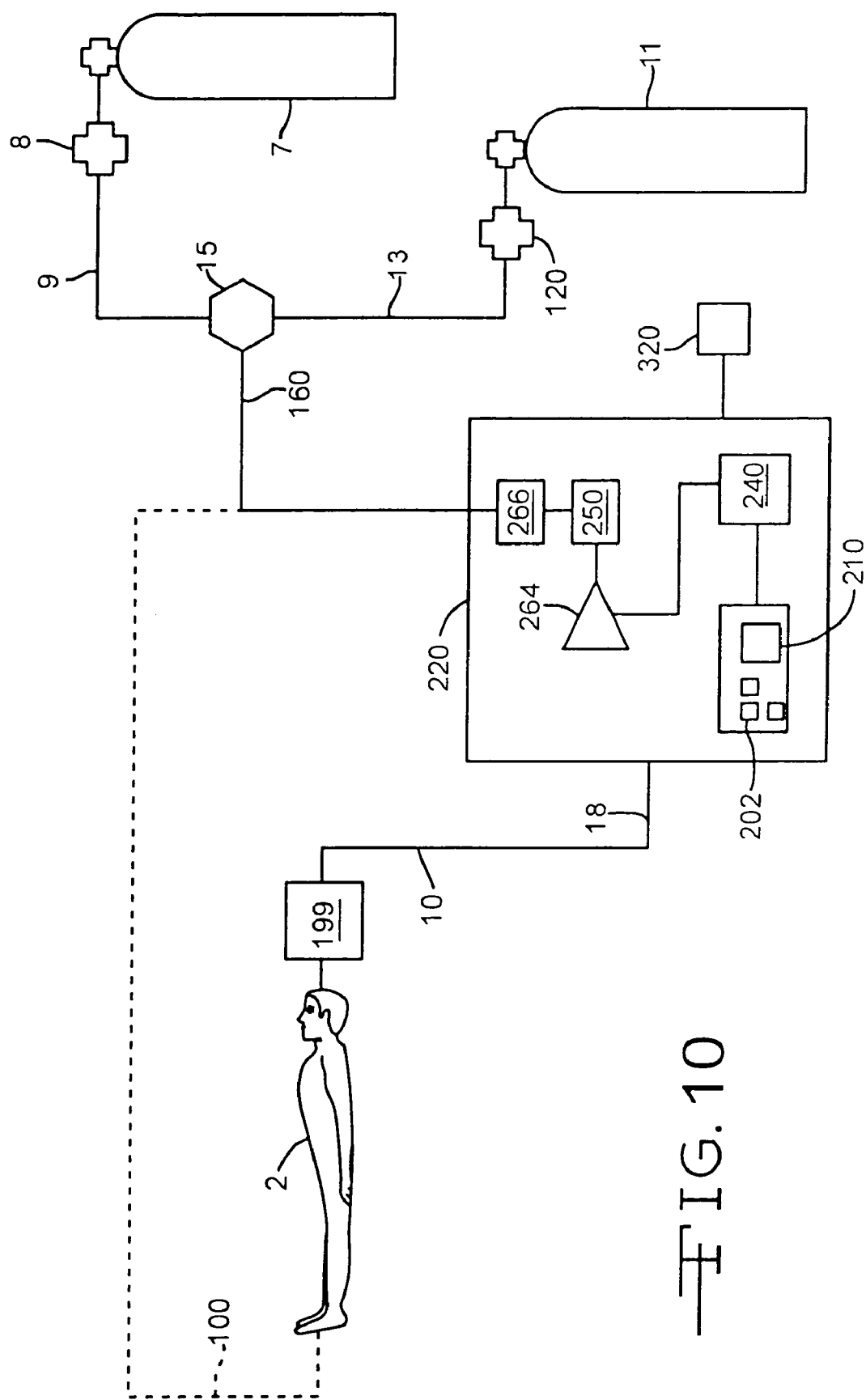
FIG. 10 is an alternative embodiment of the present invention.

FIG. 10 illustrates a block diagram representation of the device 220, which can be an alternative version of item 17. The device 220 has a power source 220 that provides sufficient voltage and charge to properly operate the device 220. The device 220 also has a main microprocessor 240 that controls the operation of a solenoid valve 260, also within the device 220. The solenoid valve 260 operates in conjunction with operating parameters that are entered via a data entry keypad 201 and the input from a pressure sensor 280.

The operating parameters and the operating status of the device 220 are displayed on an LCD display 210.

The device 220 has a pressure regulator 266. The pressure regulator 266 reduces the pressure of the nitric oxide to less than 100 psi so it can be administered to the patient 2 without damaging the patient's organs, in particular the lungs, from too much pressure.

Calibrating the flow through the solenoid valve 264 is obtained by selecting the pressure of the pressure regulator 266 and controlling the time that the solenoid valve 264 is open. Thereby, the valve 264 allows a precise amount of nitric oxide gas composition to be delivered through the gas delivery line 18, which delivers the nitric oxide to the patient's breathing orifice(s). The pressure sensor 280 is designed to detect a drop in pressure in the gas delivery line 18, when the patient initiates a breath. This pressure drop signals the main processor 240 to open the solenoid valve 264 for a preprogrammed period of time. Among the parameters that are programmed into the device are: Total Breaths, Start Delay, Pulse Time, Pulse Delay, and Re-trigger Lock.

The programmable parameters are defined as follows:

Total Breaths: This parameter is the number of breaths programmed into a run of the device 220. Each time a breath is detected as identified above, a pulse of nitric oxide gas composition is injected into the breath of patient 2. Breaths that occur during a locked out time of the predetermined time frame are not counted as breaths. After the programmed number of breaths are counted, the program stops automatically and nitric oxide gas composition is no longer injected into any breaths of the patient. This number can be set anywhere from 0 to unlimited number of breaths. If the number is set at 0 then the auto shutoff is disabled and breaths will be injected with nitric oxide until the user stops the device.

Start Delay: This parameter is the programmed delay time in minutes that the user can set. The injection of nitric oxide gas composition into each breath will begin automatically after "Start Delay" minutes. It will then continue for the number of Total Breaths and then the device 12 stops automatically.

Pulse Time: This parameter is the length of time that the solenoid valve 264 will open for delivery of nitric oxide gas composition. The resolution is 0.1 seconds and the range is 0.1 sec to 0.9 seconds. If the regulator is set at 50 psi then each second of the solenoid valve 264 opening 31 cc of nitric oxide gas composition. If the regulator pressure is set at 30 psi then each 0.1 sec solenoid valve 264 opening represents 21 cc of nitric oxide gas composition. For example, if the regulator is set at 50 psi and the pulse time is set at 0.3 seconds then each detected breath will be injected with a pulse of 0.3 seconds or about 90 cc of nitric oxide gas composition.

Pulse delay: This parameter is the length of time that the machine waits after detecting the beginning of a breath before opening the solenoid valve 264 to inject a pulse of nitric oxide gas composition. This allows the user to control the position of the bolus of nitric oxide gas composition in the breath. For example, if the user sets the solenoid valve 264 at 0.4 seconds, then 0.4 seconds after the beginning of the breath is detected the solenoid valve 264 will open to inject the nitric oxide gas composition pulse.

Retrigger Lock: This parameter is the total time that the machine will ignore new breaths beginning at the detection of a new breath. If this parameter is set at 4.5 seconds then the device 220 will wait, after detecting a breath, for 4.5 seconds before recognizing a new breath. Full or half breaths that are initiated by the patient during this lockout time will not be counted and no nitric oxide gas composition will be injected. If the breath is initiated before the lockout expires and the patient is still inhaling when the lockout expires then it will be recognized as a new breath and it will be counted and injected with nitric oxide gas composition.

The data entry keypad 202 contains five active button switches defined as follows:

START/PULSE KEY: This key is used to start a run. The user is required to confirm the start by pressing an UP key or to cancel by pressing a DOWN key. When a run is in progress, pressing this key will cause the run to pause. The run is then resumed by pressing the UP key or stopping the run by pressing the DOWN key.

UP key: This key is used to confirm the start of the run, to resume a paused run and also to increment valve changes.

DOWN key: This key is used to cancel a started run, end a paused run and also to decrement valve changes.

NEXT key: This key is used to switch screen pages on the LCD display.

PURGE key: This key is used to open the solenoid valve 264 for two seconds to purge the line. This key is not active during a run. The LCD display can display at least four screen pages, defined as follows:

Each screen page displays a status line. The status variations include NOT RUNNING, WAITING, RUNNING, PAUSED, PURGING and START Pressed.

The main screen page has a row of asterisks on the top line. This is the only screen available when the KEY switch is in the locked position. This screen displays the total breaths detected and also the total breaths that will cause the run to stop.

The second page shows two valves. The first is the START DELAY valve. When the screen first appears the blinking cursor shows the value, which can be changed by pressing either the UP or DOWN key. By pressing the NEXT key switch the cursor to the second value on the screen is TOTAL BREATHS.

The third page allows the user to change the PULSE DELAY and the PULSE TIME.

The fourth page allows the user to change the RETRIGGER LOCK.

In any case, this embodiment of the invention allows the nitric oxide gas composition to be injected into a patient's lung, preferably when the patient is inhaling, of a sufficient quantity that nitric oxide is capable of penetrating both the epithelial and capillary basement membranes to allow the nitric oxide to contact the numerous blood cells to reduce pathogens in the blood system and throughout the body.

Other embodiments of the dispenser apparatus of the nitric oxide gas are disclosed in U.S. Pat. No. 6,432,077, which is hereby incorporated by reference herein.

The dispenser can be any device that can apply nitric oxide to any object that can contain a biofilm. The object being selected from a group consisting of a medical device, a conduit for industrial, home, office space, municipal, or medical purposes, and an animal for internal and/or external applications.

Alternatively, this latest method can provide the nitric oxide gas continuously, just not when the patient 2 inhales.

In addition the gNO can be directed into application systems via pressurized cylinders to the specific target interface.

A number of experiments were undertaken to determine the efficacy of various dose concentrations of exogenously applied gaseous nitric oxide on the microorganism *Burkholderia cenocepacia*. *B. cenocepacia* is an opportunistic pathogen that plays a role in the formation of biofilms and can cause marked lung infections in cystic fibrosis patients. *B. cenocepacia* is also associated with increased rates of sepsis and death.

EXAMPLE

Objective: To determine if exposure to gaseous nitric oxide (gNO) affects the ability of *B. cenocepacia* C8963 to form a biofilm in a 96-well microtiter dish assay.

Methods: *B. cenocepacia* C8963, a non-mucoid isolate from a cystic fibrosis (CF) patient, and C9343, a mucoid isolate from the same patient, were spotted on Luria Broth agar and grown at 37° C. overnight. Luria broth containing 0.5% (w/v) casamino acids was dispensed into 96-well polypropylene microtiter dishes (100 μl per well) and the wells inoculated with the C8963 or C9343 using a pin-inoculation device. Blank wells were not inoculated. Dishes were incubated in a humidified, closed plastic container for 24 hours at 37° C. (experiment 1) or in the outer chamber of the matrix incubator (a humidified incubator with controlled air flow) for 27 hours at 37° C. (experiment 2). At 24 hours (experiment 1) or 27 hours (experiment 2), one dish was processed for staining of the bacterial biofilms. The remaining dishes were incubated in the inner treatment arms of the matrix incubator at 37° C. in the presence or absence of 200 ppm gNO. One dish for each of the conditions (+gNO or −gNO) was processed for biofilm staining at 32, 36, and 48 hours.

To stain biofilm growth, planktonic bacteria were removed from the microtitre dishes by discarding media and cells. Biofilms were washed to remove remaining non-adherent bacteria in two successive tap water washes. Water was shaken from the wells and the dishes inverted and tapped vigorously on a stack of paper towels to remove as much water as possible. Adherent growth was stained by adding 125 μl of a 0.1% (w/v) solution of crystal violet to each well and incubating at room temperature for 15 minutes. Crystal violet was discarded as for the previous washes and excess stain was removed in three successive tap-water washes. Excess water was removed by vigorous tapping as before and the stained dishes allowed to air dry.

To quantitate biofilm formation, 200 μl of 95% ethanol was added to each well, incubated at room temperature for 15 minutes, and 125 μl from each well was removed to a clean flat-bottomed polystyrene microtitre dish. The absorbance at 595 nm was read on a Bio-Rad Model 3550 Microplate Reader. The average reading from "Blank" (uninoculated) wells containing only media was subtracted from each "Test" well. The [Test-Blank] averages and standard errors of the mean (SEM) were calculated for each condition and time.

Figure 11:
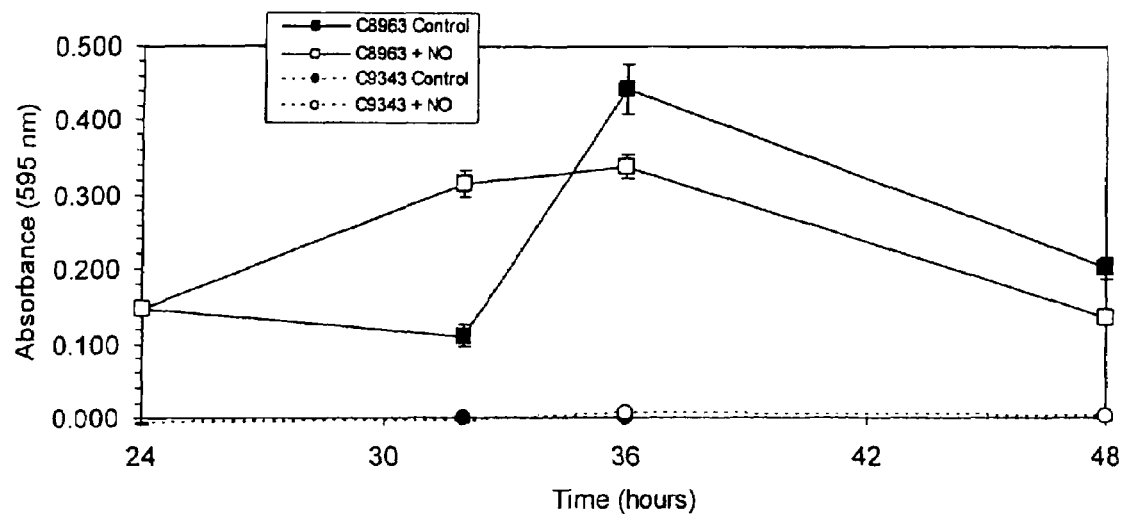
FIG. 11 is a graphical chart corresponding to experiment 1, entitled "*Burkholderia cenocepacia* C8963 & C9343 biofilm formation in presence and absence of nitric oxide", wherein *B. cenocepacia* C8963 and C9343 biofilm formation is illustrated in the presence and absence of gNO. Biofilms were allowed to grow for 24 hours in air before being grown in the presence (+NO) and absence (Control) of 200 ppm gNO. Squares represent C8963 biofilm growth and circles represent C9343 biofilm growth. Average $A_{595S}$ and SEM appear in discussion of experiment 1 below.
Figure 12:
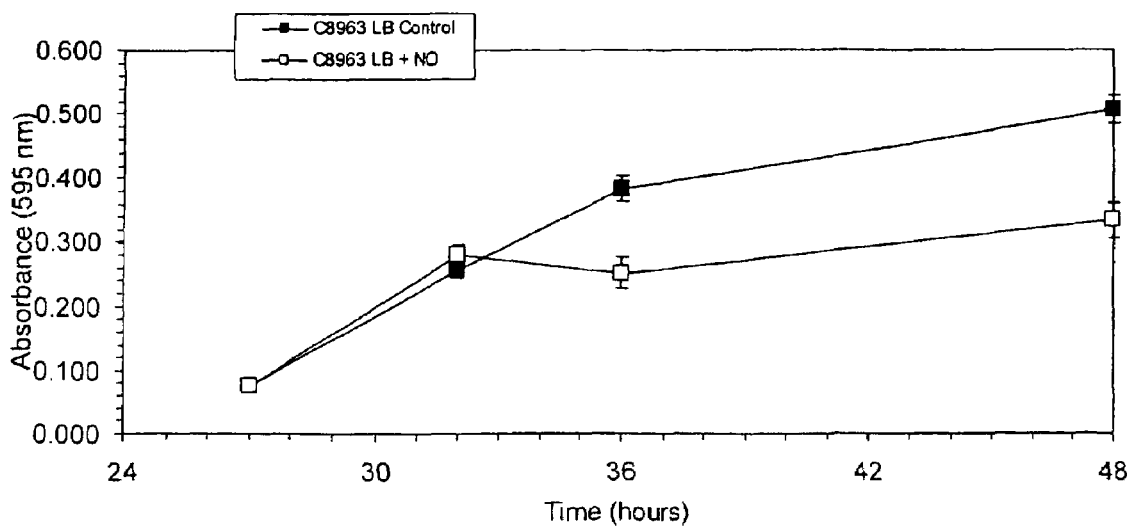
FIG. 12 is a graphical chart corresponding to experiment 2, entitled, "*Burkholderia cenocepacia* C8963 biofilm formation in presence and absence of nitric oxide", wherein *B. cenocepacia* C8963 biofilm formation is illustrated in the presence and absence of gNO. Biofilms were allowed to grow for 27 hours in air before being grown in the presence (+ NO) and absence (Control) of 200 ppm gNO. Squares represent C8963 biofilm growth and circles represent C9343 biofilm growth. Average $A_{595S}$ and SEM appear in discussion of experiment 2 below.

Results: As expected, the mucoid C9343 isolate did not form biofilm under any conditions (FIG. 11). This is consistent with its previous behavior since the mucoid exopolysaccharide interferes with adherence to surfaces (1). Overall, the non-mucoid C8963 isolate continued to form biofilm in the presence of gNO but growth was lower than in the absence of gNO. C8963 biofilm growth in the presence of gNO was greater than in the absence of gNO at 32 hours, but by 36 hours, growth in the presence of gNO was significantly lower than in the absence of gNO in both experiment 1 (FIG. 11) and experiment 2 (FIG. 12). Biofilm growth remained consistently lower in the presence of gNO for the remaining time points up to 48 hours in both experiments (FIGS. 11 and 12).

In experiment 1, maximum biofilm growth occurred at approximately 36 hours (FIG.11) but in experiment 2, maximum biofilm growth did not occur until 48 hours or more (FIG. 12).

Discussion: B. cenocepacia C9343 was a mucoid pulmonary isolate from a CF patient that was previously shown to be a poor biofilm former (1). B. cenocepacia C8963 was a non-mucoid pulmonary isolate from the same CF patient and was shown to be a competent biofilm former (1). To determine if exposure to gNO affected biofilm formation by these organisms, both were grown in the presence and absence of 200 ppm gNO. The organisms were grown for 24 hours without gNO to establish the biofilm, then exposed to gNO or air only in the final 24 hours of the assay. C9343 served as a negative control since it did not form biofilm under any condition. The presence of gNO did not induce biofilm formation by this organism. For this reason, C9343 was not included in experiment 2.

C8963 formed biofilm in two independent assays. In both cases, introduction of gNO after 24 hours (experiment 1) and 27 hours (experiment 2) resulted in increased biofilm growth at 32 hours compared to biofilm growth in the presence of the carrier gas (air). At first, gNO likely provides a source of nitrogen to the growing bacteria, and that this is advantageous while the effective concentration of gNO dissolved in the media is low. At all subsequent time points, C8963 biofilm growth was lower in the presence of gNO. This implies that once the concentration of gNO equilibrated to 200 ppm within the biofilm system, it decreased the amount of biofilm formation by C8963 compared to the carrier gas. Thus, gNO acted as a nutrient when present at a low effective concentration and as a biofilm inhibitor at higher effective concentrations.

The maximum amount of C8963 biofilm formation was higher in experiment 2 ($A_{595}$=0.507) than experiment 1 ($A_{595}$=0.441). This difference could be due to different initial inocula received or due to differences in the way the organisms were grown on the first day of the experiment. A more detailed time-course and repetition of the growth conditions from experiment 2 would answer this question.

Gaseous NO affected the biofilm growth of B. cenocepacia C8963 in two ways: at low initial concentrations it enhanced biofilm growth and at the 200 ppm final concentration it inhibited biofilm formation in the 96-well microtiter dish assay.

Chart 1. B. cenocepacia C8963 biofilm formation in the presence and absence of gNO. Biofilms were allowed to grow for 24 hours in air before being grown in the presence (+NO) and absence (Control) of 200 ppm gNO. Squares represent C8963 biofilm growth and circles represent C9343 biofilm growth. Average $A_{595s}$ and SEM appear below.

CHART 2

| B. cenocepacia C8963 biofilm formation in the presence and absence of gNO. Biofilms were allowed to grow for 27 hours in air before being grown in the presence (+ NO) and absence (Control) of 200 ppm gNO. Average $A_{595}$s and SEM appear below. | | | | |
| --- | --- | --- | --- | --- |
| Time (h) | C8 Con | C8 + NO | C8 Con SEM | C8 + NO SEM |
| 27 | 0.076 | 0.076 | 0.008 | 0.008 |
| 32 | 0.257 | 0.282 | 0.014 | 0.015 |
| 36 | 0.383 | 0.252 | 0.020 | 0.025 |
| 48 | 0.507 | 0.334 | 0.023 | 0.027 |

The term "ambient" refers to the gases that surround the targeted interface.

If the nitric oxide is exposed to blood, the nitric oxide can work within the blood for a very brief period of time until it is modified by the hemoglobin. The modification is normally when the nitric oxide attaches to the hemoglobin. Once attached, the nitric oxide is normally not able to destroy a biofilm with the present apparatus.

It is appreciated that various modifications to the inventive concepts described herein may be apparent to those of ordinary skill in the art without departing from the scope of the present invention as defined by the herein appended claims.

We claim:

1. A method of treating a bioflim comprising:
   applying gaseous nitric oxide to the biofilm to impair the bioflim.

2. The method of claim 1, wherein the bioflim was generated by a microbial organism selected from the group consisting of bacteria, protozoa, amoeba, and fungi.

3. The method of claim 1, wherein the biofilm is located on a medical device, a conduit for industrial, home, office space, municipal, or medical purposes, or an animal.

4. The method of claim 1, wherein the bioflim is located on surfaces at facilities selected from the group consisting of hospitals, laboratories, dental and/or medical offices, water treatment facilities, and water distribution facilities.

5. The method of claim 1, wherein the concentration of gaseous nitric oxide applied is greater than 100 ppm.

6. The method of claim 5, wherein the concentration of gaseous nitric oxide applied is greater than 200 ppm.

7. The method of claim 1, wherein the gaseous nitric oxide is applied to the biofllm for at least 30 minutes.

8. The method of claim 1, wherein the gaseous nitric oxide is applied to the biofilm for about 12 hours.

9. The method of claim 1, further comprising regulating the concentration of gaseous nitric oxide provided to the biofilm.

10. The method of claim 1, further comprising regulating the concentration of the gaseous nitric oxide to a closed environmental system.

11. A method for using nitric oxide gas (gNO) as a stand alone biocidal agent or in combination with any or all adjunct vehicles in the control of biofilms generated by microbial organisms, comprising:

applying gaseous nitric oxide to the biofilms.

12. The method of claim 11, wherein the biofilm was generated by a microbial organism selected from the group consisting of bacteria, protozoa, amoeba, and fungi.

13. The method of claim 11, wherein the biofilm is located on a medical device, a conduit for industrial, home, office space, municipal, or medical purposes, or an animal.

14. The method of claim 11, wherein the biofilm is located on surfaces at facilities selected from the group consisting of hospitals, laboratories, dental and/or medical offices, water treatment facilities, and water distribution facilities.

15. The method of claim 11, wherein the concentration of gaseous nitric oxide applied, is greater than 100 ppm.

16. The method of claim 15, wherein the concentration of gaseous nitric oxide applied is greater than 200 ppm.

17. The method of claim 11, wherein the gaseous nitric oxide is applied to the biofilm for at least 30 minutes.

18. The method of claim 17, wherein the gaseous nitric oxide is applied to the biofilm for about 12 hours.

19. A method of retarding the growth of a biofllm comprising:

applying gaseous nitric oxide to the biofilm.

20. The method of claim 19, wherein the biofllm was generated by a microbial organism selected from the group consisting of bacteria, protozoa, amoeba, and fungi.

21. The method of claim 19, wherein the biofilm is located on a medical device, a conduit for industrial, home, office space, municipal, or medical purposes, or an animal.

22. The method of claim 19, wherein the biofllm is located on surfaces at facilities selected from the group consisting of hospitals, laboratories, dental and/or medical offices, water treatment facilities, and water distribution facilities.

23. The method of claim 19, wherein the concentration of gaseous nitric oxide applied is greater than 100 ppm.

24. The method of claim 13, wherein the concentration of gaseous nitric oxide applied is greater than 200 ppm.

25. The method of claim 19, wherein the gaseous nitric oxide is applied to the biofllm for at least 30 minutes.

26. The method of claim 25, wherein the gaseous nitric oxide is applied to the biofilm for about 12 hours.

* * * * *